US012758175B2

(12) United States Patent
Sugiyama

(10) Patent No.: US 12,758,175 B2
(45) Date of Patent: Oct. 13, 2026

(54) WALL THICKNESS ESTIMATION METHOD, RECORDING MEDIUM, WALL THICKNESS ESTIMATION DEVICE, AND WALL THICKNESS ESTIMATION SYSTEM

(71) Applicant: OSAKA UNIVERSITY, Osaka (JP)

(72) Inventor: Yoshie Sugiyama, Osaka (JP)

(73) Assignee: OSAKA UNIVERSITY, Osaka (JP)

( * ) Notice: Subject to any disclaimer, the term of this patent is extended or adjusted under 35 U.S.C. 154(b) by 130 days.

(21) Appl. No.: 18/271,977

(22) PCT Filed: Feb. 18, 2022

(86) PCT No.: PCT/JP2022/006662
§ 371 (c)(1),
(2) Date: Jul. 12, 2023

(87) PCT Pub. No.: WO2022/190821
PCT Pub. Date: Sep. 15, 2022

(65) Prior Publication Data

US 2024/0081767 A1 Mar. 14, 2024

(30) Foreign Application Priority Data

Mar. 9, 2021 (JP) ................................ 2021-036850

(51) Int. Cl.
*A61B 6/00* (2024.01)
*A61B 6/50* (2024.01)
*A61B 5/055* (2006.01)

(52) U.S. Cl.
CPC ............ *A61B 6/5217* (2013.01); *A61B 6/504* (2013.01); *A61B 5/055* (2013.01)

(58) Field of Classification Search
CPC ...................................................... A61B 6/504
See application file for complete search history.

(56) References Cited

U.S. PATENT DOCUMENTS

2015/0038860 A1* 2/2015 Fonte .................. A61B 6/5217 600/505
2019/0087957 A1* 3/2019 Burris ................ A61B 5/02014

FOREIGN PATENT DOCUMENTS

JP 2013-118932 6/2013

OTHER PUBLICATIONS

International Search Report issued May 17, 2022 in corresponding International Application No. PCT/JP2022/006662.

* cited by examiner

*Primary Examiner* — Michael T Rozanski
*Assistant Examiner* — Aminah Asghar
(74) *Attorney, Agent, or Firm* — Wenderoth, Lind & Ponack, L.L.P.

(57) ABSTRACT

A wall thickness estimation method includes: obtaining behavioral information based on a video in which an organ wall or a blood vessel wall is captured using four-dimensional angiography, the behavioral information being numerical information about changes over time in a position of each of a plurality of predetermined points in the organ wall or the blood vessel wall; generating, based on the behavioral information obtained in the obtaining, estimation information that visualizes a strain of each of the plurality of predetermined points for estimating a thickness of the organ wall or a thickness of the blood vessel wall; and outputting the estimation information generated in the generating.

5 Claims, 16 Drawing Sheets

WALL THICKNESS ESTIMATION METHOD, RECORDING MEDIUM, WALL THICKNESS ESTIMATION DEVICE, AND WALL THICKNESS ESTIMATION SYSTEM

TECHNICAL FIELD

The present invention relates to a wall thickness estimation method and the like. The method is for estimating a thickness of an organ wall or a thickness of a blood vessel wall.

BACKGROUND ART

A cerebral aneurysm, which is one example of a vascular disease, is an extremely high-risk disease with a fatality rate of more than 50% once it ruptures, and the cerebral aneurysm is also a socially significant disease due to its high rate of aftereffect. For this reason, prophylactic treatment (preemptive medicine) to prevent rupture of cerebral aneurysms is very important, and proper therapeutic intervention is essential.

For proper treatment, it is useful to know information about (for example, the thickness of) the wall of the cerebral aneurysm. This is because it is known that a cerebral aneurysm is more likely to rupture in areas with thin walls than in areas with thick walls. However, even within a single aneurysm, the geometry, including the thickness, of the aneurysm wall varies from aneurysm to aneurysm.

It is therefore difficult even for experts to infer information about the geometry, including the thickness, of the aneurysm wall only from the shape of the lumen or the like of the aneurysm wall obtained by computed tomography (CT), magnetic resonance imaging (MRI), and magnetic resonance angiography (MRA).

For example, one known method of measuring the thickness of the wall of a cerebral aneurysm is imaging or visual inspection in craniotomy performed by a doctor. However, this method is highly invasive, places a heavy burden on the patient, and is not a method by which the thickness of the wall of a cerebral aneurysm can be easily measured.

One example of a known minimally invasive method of measuring the thickness of a blood vessel wall, such as the wall of a cerebral aneurysm, is the ultrasonic diagnostic apparatus disclosed in Patent Literature (PTL) 1. PTL 1 discloses an ultrasonic diagnostic apparatus that generates image data using ultrasonic signals and displays information about the thickness of a blood vessel wall of a subject based on the image data.

CITATION LIST

Patent Literature

[PTL 1] Japanese Unexamined Patent Application Publication No. 2013-118932

SUMMARY OF INVENTION

Technical Problem

Unfortunately, the image data obtained using the conventional technique disclosed in PTL 1 is less precise, and therefore, it is difficult to obtain highly accurate information about the blood vessel wall. Furthermore, it is difficult to obtain highly accurate information about not only the blood vessel wall but also an organ wall in a human body and propose information for providing specific treatments for organ diseases or blood vessel diseases according to the conventional technique.

In view of this, the present invention has an object to provide a method and the like that can generate highly accurate information about the organ wall or the blood vessel wall using a minimally invasive method, thereby providing useful information for applying specific treatments for organ diseases or blood vessel diseases.

Solution to Problem

A wall thickness estimation method according to an aspect of the present invention includes: obtaining behavioral information based on a video in which an organ wall or a blood vessel wall is captured using four-dimensional angiography, the behavioral information being numerical information about changes over time in a position of each of a plurality of predetermined points in the organ wall or the blood vessel wall; generating, based on the behavioral information obtained in the obtaining, estimation information that visualizes a strain of each of the plurality of predetermined points for estimating a thickness of the organ wall or a thickness of the blood vessel wall; and outputting the estimation information generated in the generating.

A recording medium according to one aspect of the present invention is a non-transitory computer-readable recording medium having a program recorded thereon. The computer program is for causing a computer to execute the above-described wall thickness estimation method.

Furthermore, a wall thickness estimation device according to an aspect of the present invention includes: an obtainer which obtains behavioral information based on a video in which an organ wall or a blood vessel wall is captured using four-dimensional angiography, the behavioral information being numerical information about changes over time in a position of each of a plurality of predetermined points in the organ wall or the blood vessel wall; a generator which generates, based on the behavioral information obtained by the obtainer, estimation information that visualizes a strain of each of the plurality of predetermined points for estimating a thickness of the organ wall or a thickness of the blood vessel wall; and an outputter which outputs the estimation information generated by the generator.

Furthermore, a wall thickness estimation system according to an aspect of the present invention includes: the wall thickness estimation device described above; a video information processing device which obtains the video, generates the behavioral information, and outputs the behavioral information to the obtainer; and a display which displays the estimation information output by the outputter.

Advantageous Effects of Invention

With the blood vessel wall thickness estimation method and the like according to the present invention, it is possible to generate highly accurate information about the organ wall or the blood vessel wall using a minimally invasive method, thereby providing useful information for applying specific treatments for organ diseases or blood vessel diseases.

DESCRIPTION OF EMBODIMENTS

Hereinafter, embodiments are described with reference to the drawings. Each of the following embodiments describes a general or specific example. The numerical values, shapes, materials, elements, the arrangement and connection of the elements, steps, the order of the steps etc., presented in the following embodiments are mere examples, and do not limit the scope of the present invention. Among the elements in the following embodiments, those not recited in any one of the independent claims are described as optional elements.

It is to be noted that the diagrams are schematic drawings, and are not necessarily exactly illustrated. In the diagrams, substantially the same elements are assigned with the same numerical references. Accordingly, overlapping descriptions thereof are omitted or simplified.

Embodiment

[Configuration of Wall Thickness Estimation System]

Figure 1:
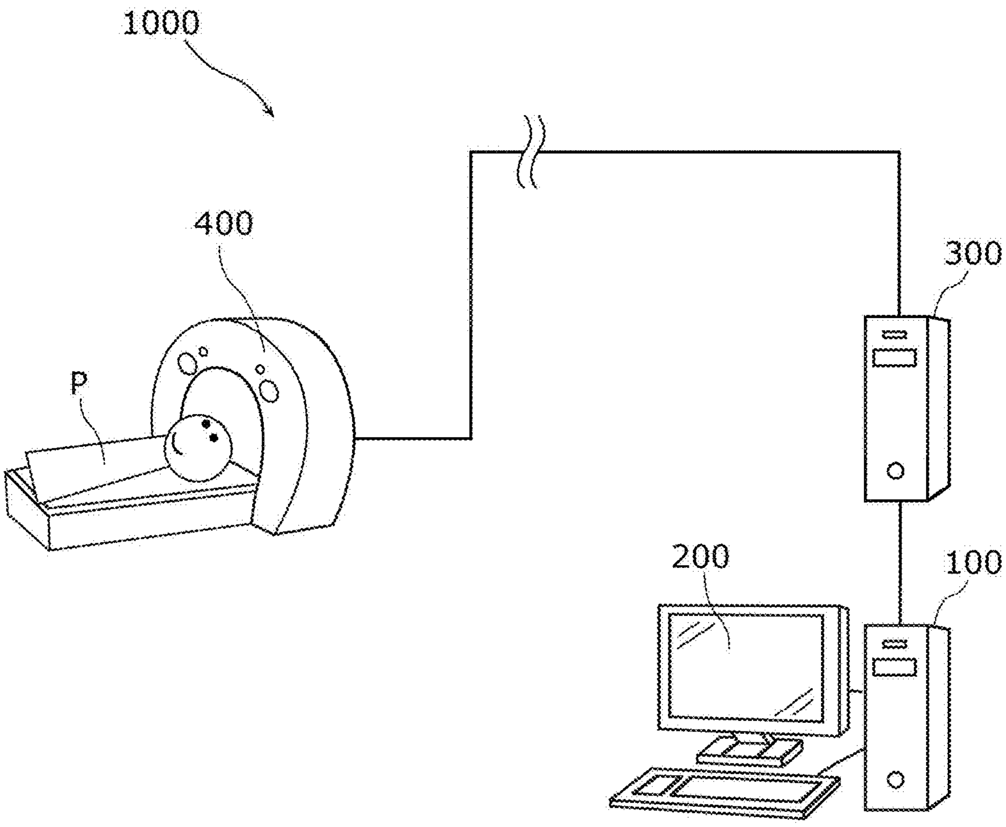
FIG. 1 is a diagram illustrating the configuration of a wall thickness estimation system according to an embodiment.

First, the configuration of wall thickness estimation system 1000 according to an embodiment is described. FIG. 1 is a diagram illustrating the configuration of wall thickness estimation system 1000 according to the embodiment.

Wall thickness estimation system 1000 is a system that uses four-dimensional angiography to obtain behavioral information, which is numerical information about changes over time in the position of each of predetermined points, from a video in which an organ wall or a blood vessel wall of subject P is captured. Wall thickness estimation system 1000 further generates, for each position, estimation information for estimating the thickness of the organ wall or the thickness of the blood vessel wall based on the behavioral information obtained. For example, wall thickness estimation system 1000 estimates a thickness of a cerebral aneurysm which is one example of a blood vessel wall in subject P.

Four-dimensional angiography is a technique that adds a time axis to three-dimensional angiography. Three-dimensional angiography is a technique that collects three-dimensional data on blood vessels using an X-ray CT device or an MRI device, and extracts vascular information. Four-dimensional angiography using an X-ray CT device is also referred to as four-dimensional computed tomography angiography (4DCTA).

A video is obtained through four-dimensional angiography. The video is a time series of three or more still images, and may be, for example, a video obtained over n pulses of the heart (n is a natural number). For example, the video may be a video within a predetermined time period. For example, the predetermined time period may be m seconds (m is a natural number).

Here, an organ wall is a wall of an organ, and organs include chest organs and abdominal organs. For example, chest organs include a heart, lungs, etc., and abdominal organs include a stomach, intestines, a liver, kidneys, a pancreas, etc., but examples of chest organs and abdominal organs are not limited thereto. In addition, organs may include chest organs each having a lumen and abdominal organs each having a lumen.

A wall of an organ may be, for example, a wall that divides the organ and other organs. As one example, when the organ is a heart, an organ wall is a wall defined by muscles (myocardium) that divides the heart and the other organs. The organ wall may be, for example, a wall that divides regions in the organ. As one example, when the organ is a heart, the organ wall is the interventricular septum that divides the left ventricle and the right ventricle which are examples of regions in the heart.

The thickness of the blood vessel wall may be the thickness of a wall of the blood vessel that is an artery or a vein and may be the thickness of the wall of an aneurysm or a wall of a varicose vein. For example, the thickness of the blood vessel wall may be the thickness of the wall of a cerebral aneurysm, an aortic aneurysm, or visceral aneurysm.

As illustrated in FIG. 1, wall thickness estimation system 1000 includes wall thickness estimation device 100, display 200, video information processing device 300, and video capturing device 400.

Video capturing device 400 is a device that generates a video in which an organ wall or a blood vessel wall is captured using four-dimensional angiography. Video capturing device 400 is, for example, an X-ray CT device or an MRI device. In this embodiment, video capturing device 400 is an X-ray CT device, and video capturing device 400 includes an X-ray tube that irradiates X-rays, a detector that receives signals, and a computer.

The detector is located opposite the X-ray tube and detects the X-rays after they have passed through the body of subject P. Using the fact that the absorption of X-rays differs depending on the part of the body of subject P, the computer generates a video including the organ wall or the blood vessel wall in a specific part of the body of subject P. It is to be noted that video capturing device 400 has a function of measuring and obtaining an electrocardiographic complex of subject P.

Unlike techniques such as abdominal operation, open heart surgery, and craniotomy, the technique of using an X-ray CT device or an MRI device and four-dimensional angiography is a minimally invasive technique because it does not require an incision or the like that places a large burden on the body of subject P. Moreover, the technique of using the X-ray CT device or the MRI device and four-dimensional angiography can generate highly precise videos.

Video information processing device 300 obtains a video in which an organ wall or a blood vessel wall is captured using four-dimensional angiography generated by video capturing device 400, and generates behavioral information which is numerical information about changes over time in the position of each of a plurality of predetermined points in the organ wall or the blood vessel wall. In other words, the behavioral information is information based on the video in which the organ wall or the blood vessel wall is captured obtained using four-dimensional angiography.

For example, the behavioral information is numerical information in which a plurality of pairs of (i) a specific time in the video and (i) the three-dimensional coordinate position of each of a plurality of predetermined points in the organ wall or the blood vessel wall at that specific time are arranged according to the passage of time in which the heart pulsates one time in the video. It is to be noted that the plurality of predetermined points means very small regions.

Video information processing device 300 outputs the behavioral information to wall thickness estimation device 100. Video information processing device 300 is, for example, a personal computer, but may also be a server with high computing performances that is connected to a network.

Wall thickness estimation device 100 obtains the behavioral information generated by video information processing device 300, generates, for each position, estimation information for estimating the thickness of the organ wall or the thickness of the blood vessel wall based on the obtained behavioral information, and outputs the generated estimation information to display 200. Wall thickness estimation device 100 is, for example, a personal computer, but may also be a server with high computing performances that is connected to a network.

Display 200 displays the estimation information output from wall thickness estimation device 100. Specifically, display 200 is a monitor including, for example, a liquid crystal panel or an organic electroluminescent (EL) panel. A television, a smartphone, or a tablet terminal may be used as display 200.

Wall thickness estimation device 100, display 200, and video information processing device 300 may be connected by wire or wirelessly, as long as they can send and receive the behavioral information or the estimation information.

Video information processing device 300 obtains a video in which an organ wall or a blood vessel wall is captured, and generates behavioral information which is numerical information about changes over time in the position of each of a plurality of predetermined points in the organ wall or the blood vessel wall. Wall thickness estimation device 100 obtains the behavioral information generated by video information processing device 300, and generates, for each position, estimation information for estimating the thickness of the organ wall or the blood vessel wall based on the obtained behavioral information. Wall thickness estimation device 100 further outputs the generated estimation information to display 200.

As a result, in wall thickness estimation system 1000, a video in which the organ wall or the blood vessel wall is captured is obtained using the minimally invasive method. Furthermore, wall thickness estimation system 1000 can generate, for each position, estimation information for estimating the thickness of the organ wall or the thickness of the blood vessel wall using the behavioral information related to the video. Therefore, wall thickness estimation system 1000 can generate highly accurate information about the wall thickness in the vicinity of each of a plurality of predetermined points in the organ wall or the blood vessel wall.

Next, the functional configuration of wall thickness estimation device 100 according to the embodiment is described in detail.

Figure 2:
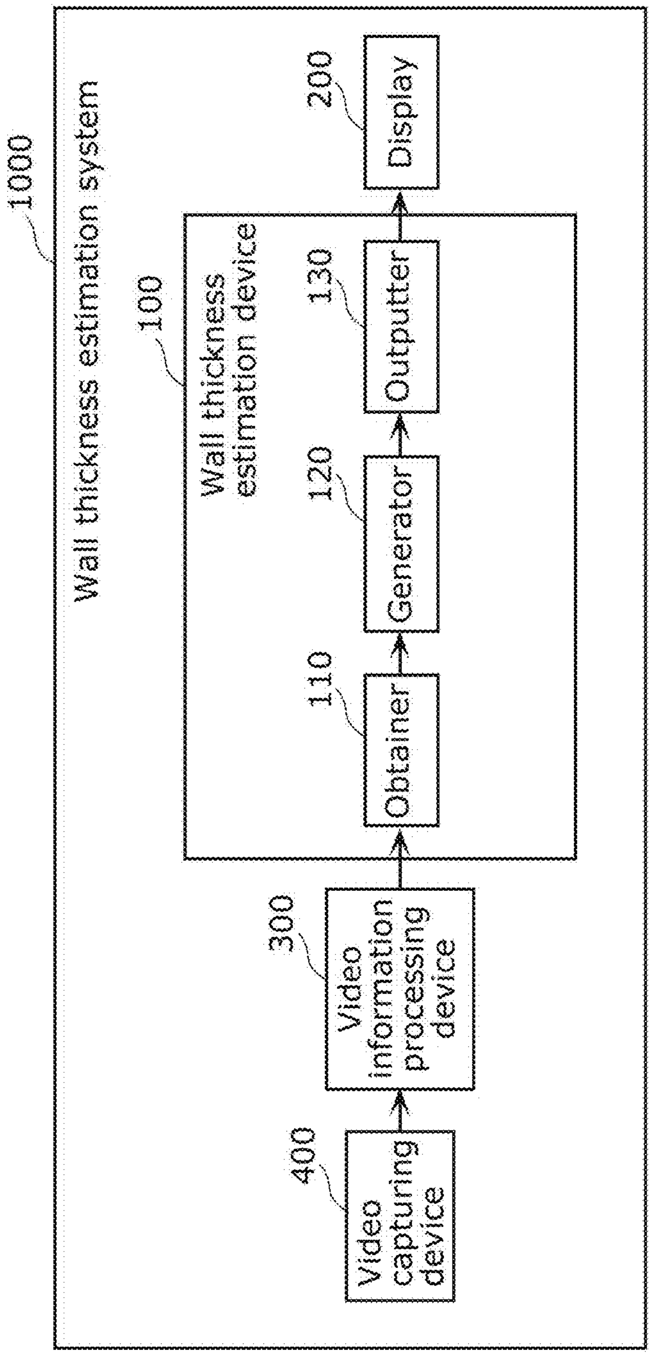
FIG. 2 is a block diagram illustrating the characteristic functional configuration of a wall thickness estimation device according to the embodiment.

FIG. 2 is a block diagram illustrating the characteristic functional configuration of wall thickness estimation device 100 according to the embodiment. Wall thickness estimation device 100 includes obtainer 110, generator 120, and outputter 130.

Obtainer 110 obtains behavioral information which is numerical information about changes over time in position of each of a plurality of predetermined points in an organ wall or a blood vessel wall, based on a video in which the organ wall or the blood vessel wall is captured obtained using four-dimensional angiography. Specifically, obtainer 110 obtains behavioral information generated by video information processing device 300. Obtainer 110 is, for example, a communication interface for performing wired or wireless communication.

Generator 120 generates, for each position, estimation information for estimating the thickness of the organ wall or the blood vessel wall based on the behavioral information obtained by obtainer 110. The estimation information is information that visualizes the strain of each of the plurality of predetermined points in the organ wall or the blood vessel wall.

The estimation information is, for example, image data obtained by schematically illustrating information about the strain of each of the plurality of predetermined points. It is to be noted that a method of generating the estimation information is described later with reference to FIGS. 6 and 7. Generator 120 is specifically implemented as, a processor, a microcomputer, or a dedicated circuit that executes a program.

Here, a description is given of an Inventors' hypothesis regarding the estimation information generated by generator 120. As described above, the estimation information is information that visualizes the strain of each of the plurality of predetermined points for estimating the thickness of the organ wall or the thickness of the blood vessel wall. The Inventors have performed tests based on the hypothesis that the strain and the thickness of the organ wall or the thickness of the blood vessel wall at each of the plurality of predetermined points in the organ wall or the blood vessel wall have a correlation with each other.

In other words, based on the hypothesis, the thickness of the organ wall or the thickness of the blood vessel wall is smaller as the strain is larger, and the thickness of the organ wall or the thickness of the blood vessel wall is larger as the strain is smaller. If the hypothesis is true, it is possible to estimate the thickness of the organ wall or the thickness of the blood vessel wall by obtaining the estimation information according to the embodiment.

Outputter 130 outputs the estimation information generated by generator 120. Outputter 130 may output the estimation information generated by generator 120 to display 200. Outputter 130 is, for example, a communication interface for performing wired or wireless communication.

Next, the plurality of predetermined points in information about the behavioral information is described with reference to FIGS. 3 to 5. The blood vessel wall is described in the embodiment, but the same description applies to the organ wall. Here, the blood vessel wall is aneurysm wall 11 of cerebral aneurysm 10.

Figure 3:
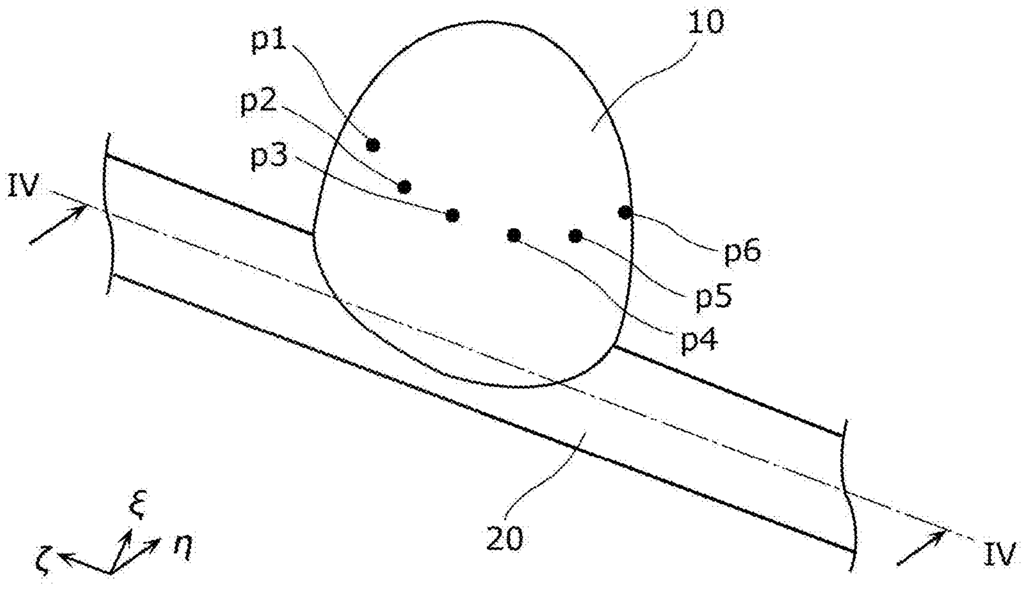
FIG. 3 is a perspective view of a cerebral aneurysm according to the embodiment.
Figure 4:
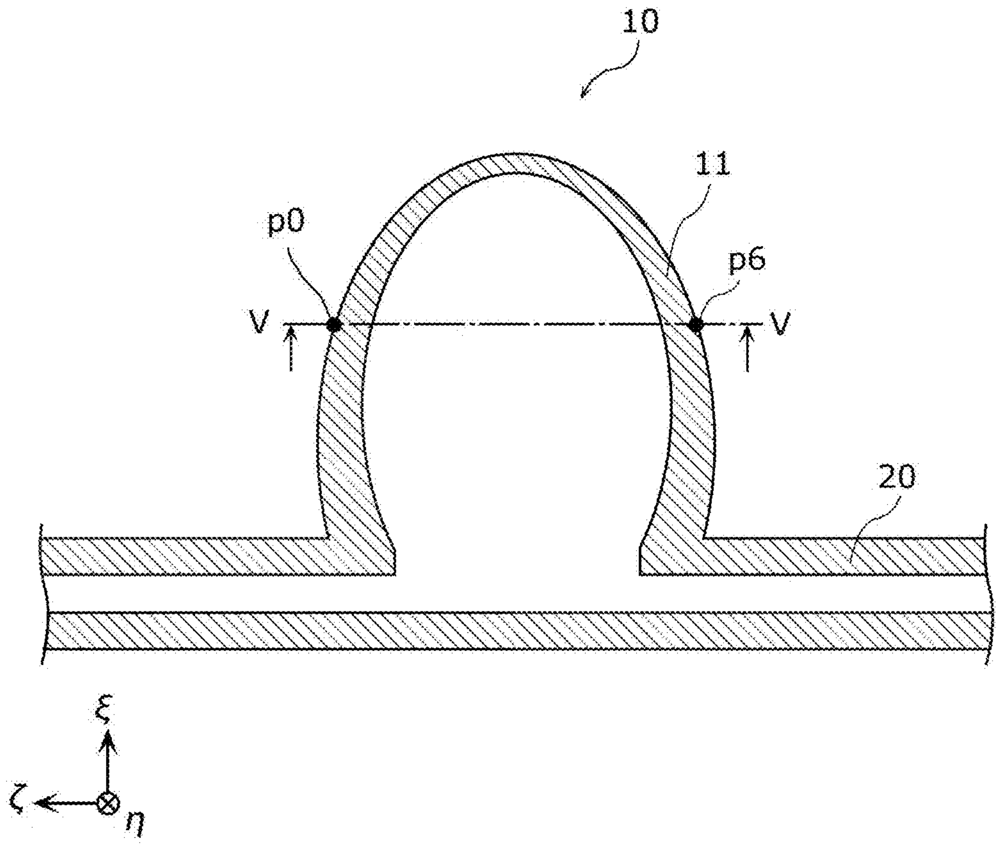
FIG. 4 is a cross sectional view of a cerebral aneurysm according to the embodiment taken at line IV-IV in FIG. 3.
Figure 5:
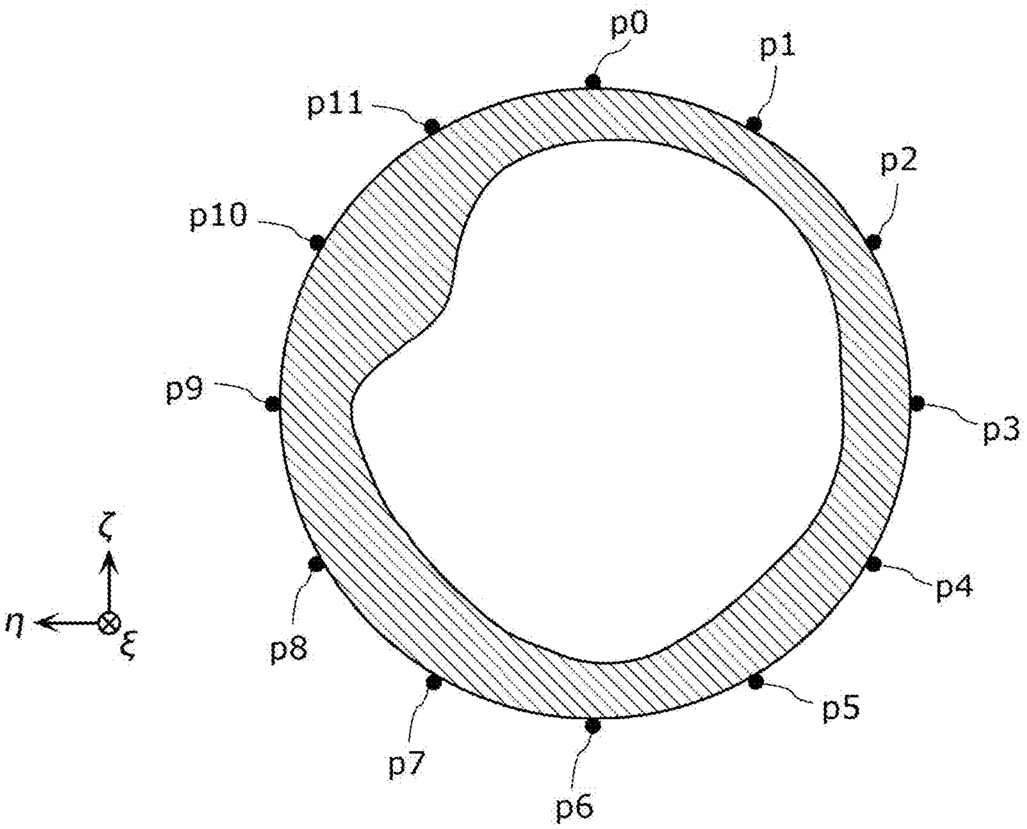
FIG. 5 is a cross sectional view of the cerebral aneurysm according to the embodiment taken at line V-V in FIG. 4.

In FIGS. 3 to 5, the ξ-axis positive direction is the direction in which cerebral aneurysm 10 extends from parent blood vessel 20, the ζ-axis is the direction in which parent blood vessel 20 extends, and the q-axis is the direction extending orthogonally to the ξ- and ζ-axes.

FIG. 3 is a perspective view of cerebral aneurysm 10 according to the embodiment. FIG. 4 is a cross sectional view of cerebral aneurysm 10 according to the embodiment taken at line IV-IV in FIG. 3. Parent blood vessel 20 is one blood vessel among the arteries in the brain of subject P. Cerebral aneurysm 10 is an aneurysm in which a portion of parent blood vessel 20 has bulged, extending in the ξ-axis direction from parent blood vessel 20.

FIG. 5 is a cross sectional view of cerebral aneurysm 10 according to the embodiment taken at line V-V in FIG. 4.

As FIG. 5 illustrates, in the cross section of cerebral aneurysm 10, points are provided in the respective 0 o'clock direction to 11 o'clock direction so as to correspond to the points of time on a clock face. Point p0 is provided in the 0 o'clock direction, and points p1 to P11 are provided in the respective 1 o'clock direction to 11 o'clock direction. In other words, twelve predetermined points are provided at the outer periphery of cerebral aneurysm 10 in the cross sectional view of cerebral aneurysm 10.

It is to be noted that the number of predetermined points is not limited thereto, and for example 10 to 1000 predetermined points may be provided at the outer periphery of cerebral aneurysm 10 in the cross section of cerebral aneurysm 10. Alternatively, although one cross section is used in this embodiment, the number of cross sections is not limited thereto. A plurality of cross sections (for example, a certain number of cross sections selected from 10 to 1000 cross sections) may be used. Furthermore, for example, 10 to 1000 predetermined points may be provided at the outer periphery of cerebral aneurysm 10 in each of the cross sections of cerebral aneurysm 10. In this case, 3000 to 200000 predetermined points are provided for cerebral aneurysm 10. In addition, the plurality of predetermined points in the blood vessel wall are not limited to the above points described above, and can be selected from two or more points in the blood vessel wall. It is to be noted that the number of predetermined points is not limited to the number selected from 3000 to 200000, and that the number smaller than 3000 or the number larger than 200000 may be selected.

The plurality of predetermined points in the blood vessel wall (aneurysm wall 11) in this embodiment are point p0 to point 11 as described above. In other words, the total number of the plurality of predetermined points present in aneurysm wall 11 is 12.

At each of these 12 predetermined points, obtainer 110 obtains behavioral information, which is numerical information about changes over time in position. Based on this behavioral information, generator 120 generates, for each position, estimation information for estimating the thickness of aneurysm wall 11 in the vicinity of a predetermined point.

In the present embodiment, the behavioral information is numerical information about changes over time in position during a certain period of time. A certain period of time is, for example, the duration of one pulsation of the heart. Furthermore, the duration of one pulsation of the heart is divided evenly into 100 steps.

It is to be noted that the duration of one pulsation of the heart is not limited thereto. The duration may be divided evenly into a certain number of steps that is selected from 10 to 1000000 steps. The number of steps is not limited to the number selected from 10 to 1000000 steps, and the number smaller than 10 or the number larger than 1000000 may be selected. Here, the point in time when the pulsation starts is 0th step, and the point in time when the pulsation ends is 100th step. In addition, the duration of one pulsation of the heart is not limited thereto. The duration is selected freely.

Accordingly, the behavioral information includes information about the ξ-, η-, and ζ-axis positions of the 12 predetermined points at the respective 0 to 100 steps. In other words, the behavioral information is data which is of each of the 12 predetermined positions and is a set of a point of time and coordinate positions (the ξ-, η-, and ζ-axis positions) at the point of time. Stated differently, the behavioral information includes time evolution data.

The certain period of time may be a specific number of seconds, for example, 1 second, 5 seconds, or 10 seconds. The certain period of time may be subdivided in any manner as long as it is three or more divisions. For example, unlike the above example, the certain period of time may be divided by a number of steps other than 100. Furthermore, the certain period of time does not always need to be divided evenly.

[Steps of Processing in Wall Thickness Estimation Method]

Figure 6:
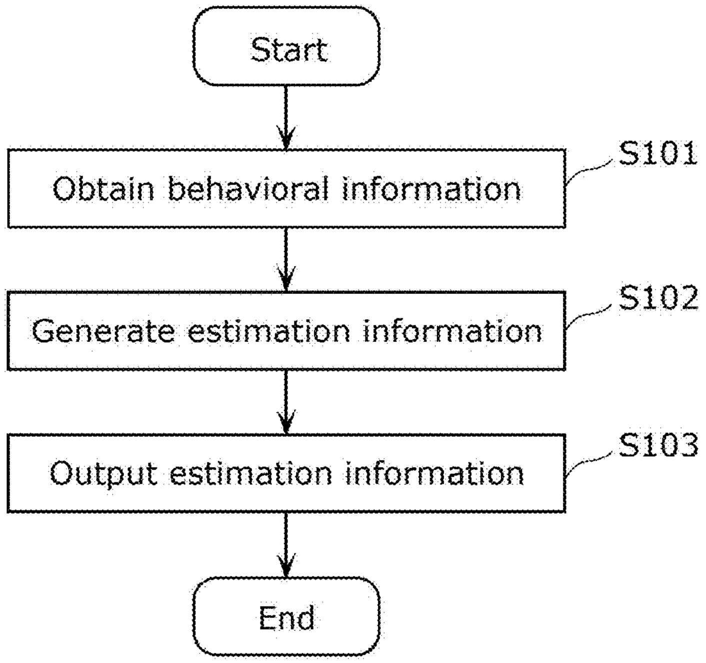
FIG. 6 is a flowchart illustrating steps of processing in which the wall thickness estimation device according to the embodiment estimates the thickness of a wall of a cerebral aneurysm.

Next, specific steps of processing in the wall thickness estimation method that is performed by wall thickness estimation device 100 is described. Although a description is given of a case of a blood vessel wall, the same description applies also to a case of an organ wall. FIG. 6 is a flowchart illustrating steps of processing in which wall thickness estimation device 100 according to the embodiment estimates the thickness of aneurysm wall 11 of cerebral aneurysm 10.

Obtainer 110 obtains behavioral information via video information processing device 300. The behavioral information is numerical information about changes over time in the position of each of a plurality of predetermined points in aneurysm wall 11 of cerebral aneurysm 10 of subject P (obtaining step S101).

Next, generator 120 generates estimation information which is information that visualizes the strain of each of the plurality of predetermined points for estimating the thickness of the blood vessel wall from the behavioral information obtained by obtainer 110 in obtaining step S101 (generating step S102). The processing performed by generator 120 is described more specifically below.

First, based on the behavioral information, generator 120 calculates the strain in each of the plurality of predetermined points.

Here, generator 120 calculates the strain using the data of points of time and positions included in the behavioral information. The strain calculation method is not particularly limited, and a publicly known method is used. For example, the strain at a single point may be calculated based on the change from a positional relationship between two points which are a first point (for example, point p1) and a second point (for example, point p2) adjacent to the first point at a point of time (for example, the 10th step) to a positional relationship between the two points at a next point of time (for example, the 11th step). In addition, a method of calculating a strain using a local plane formed by clusters of the respective predetermined points may be used.

Figure 7:
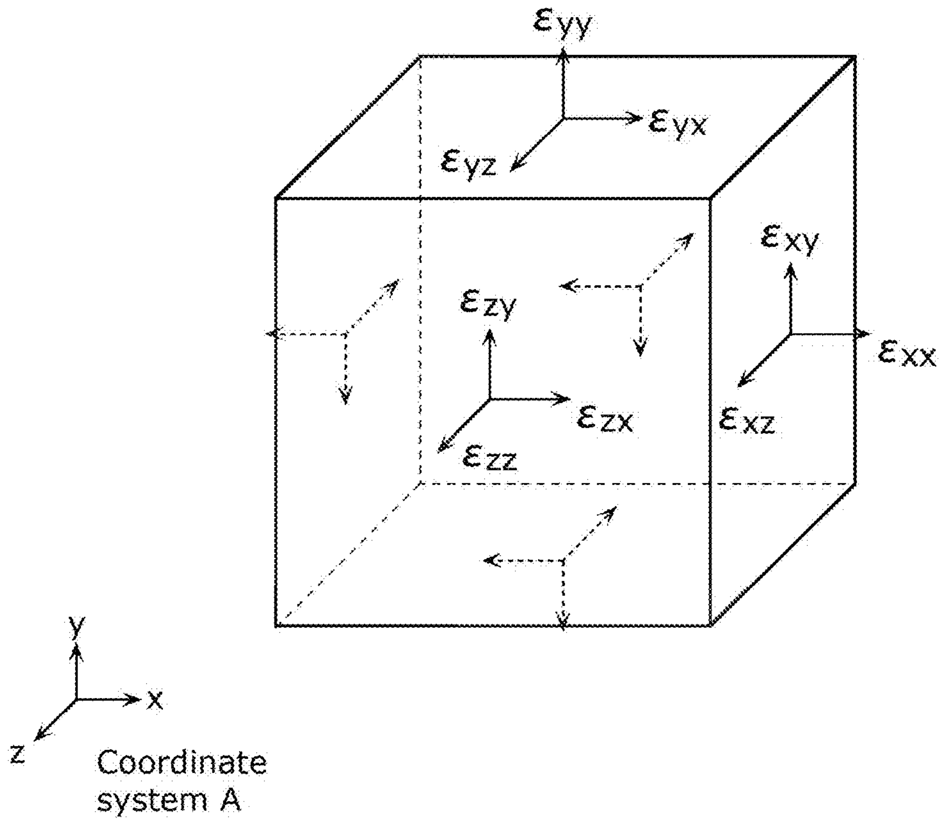
FIG. 7 is a diagram for explaining strains at predetermined points according to the embodiment.
Figure 8:
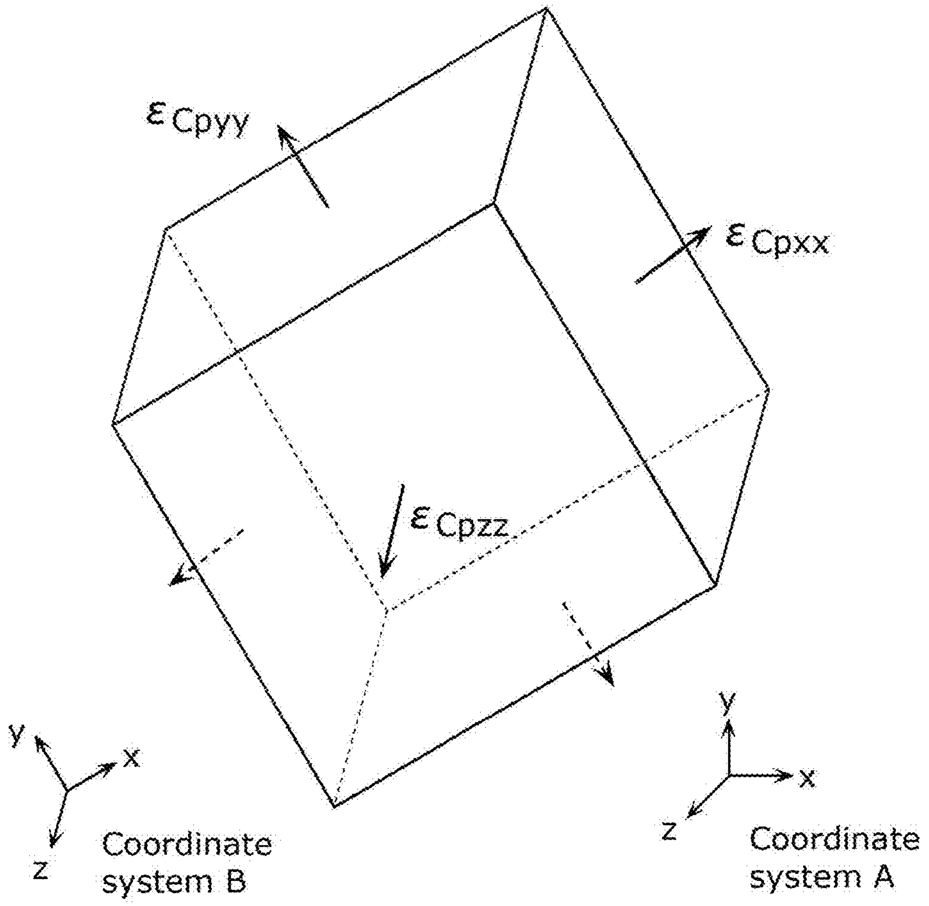
FIG. 8 is another diagram for explaining strains at predetermined points according to the embodiment.

Furthermore, strains are described with reference to FIGS. 7 and 8. FIG. 7 is a diagram for explaining strains in predetermined points according to the embodiment. FIG. 8 is a diagram for explaining strains in predetermined points according to the embodiment.

In this embodiment, each of the predetermined points is regarded as a minute cube, and the strain is calculated in the minute cube. It is to be noted that the cube illustrated in each of FIGS. 7 and 8 corresponds to the minute cube. First, as illustrated in FIG. 7, a minute cube is disposed such that the coordinate axes of a predetermined orthogonal coordinate system (coordinate system A) constitute surface normals.

At this time, the strains of a total of 9 components including the vertical strains of 3 components and sharing strains of 6 components relative to the surfaces of the minute cube are calculated. It is to be noted that the vertical strains of the 3 components are εxx, εyy, and εzz, and the sharing strains of 6 components are εxy, εxz, εyx, εyz, εzx, and εzy.

Furthermore, the coordinate system obtained by rotating the cube so as to make the values of the sharing strains of the 6 components to be 0 is determined as coordinate system B. It is to be noted that the coordinate axes in coordinate system B correspond to the surface normals of the rotated minute cube. The respective vertical strains of the 3 components are main strains, and the main strain having the maximum value among the vertical strains of the 3 components is determined to be the maximum main strain.

In this way, based on the behavioral information, generator 120 calculates the vertical strains of the respective predetermined points. It is to be noted that, for each of the predetermined points, the point of time and the vertical strains of the 3 components at the point of time are associated with each other.

Generator 120 generates estimation information using the strain (specifically, the maximum main strain) calculated as described above. As one example, the estimation information here is image data in which information relating to the calculated maximum main strain is schematically illustrated.

Next, outputter 130 outputs the estimation information generated by generator 120 (outputting step S103). In outputting step S103, outputter 130 transmits, for example, the image data generated by generator 120 in generating step S102 to display 200.

Display 200 obtains the image data output by outputter 130 and displays an image based on the image data.

Wall thickness estimation device 100 may execute the wall thickness estimation method by reading a computer program recorded on a computer-readable recording medium such as a CD-ROM.

[Relationship Between Estimation Information and Thickness of Blood Vessel Wall]

Next, the relationship between the estimation information (more specifically, the calculated strain) and the thickness of the blood vessel wall is described using a case of a symptom (hereinafter referred to as a case) regarding a cerebral aneurysm.

Here, in cerebral aneurysm 10*a* in the case, main strains are calculated, and the estimation information is generated by the maximum main strain among the main strains. It is to be noted that, in the present embodiment, the maximum number of points within the calculation capacity of wall thickness estimation device 100, for example, 100000 predetermined points are used as the number of predetermined points. It is to be noted that the number of predetermined points is not limited to 100000, and that the number lager than 100000 may be selected. The maximum main strain of each of the plurality of (for example, 100000) predetermined points is calculated.

Figure 9:
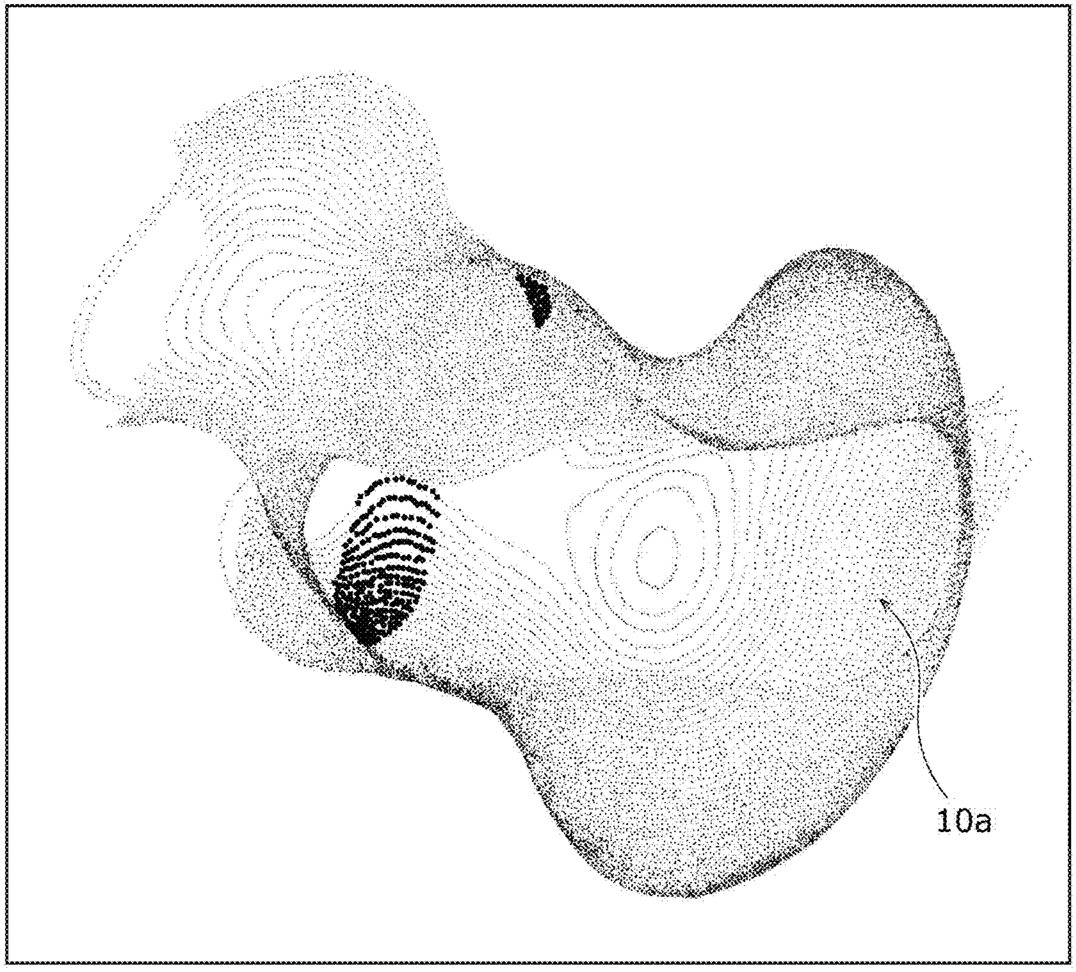
FIG. 9 is a diagram indicating an example of estimation information according to the embodiment.
Figure 10:
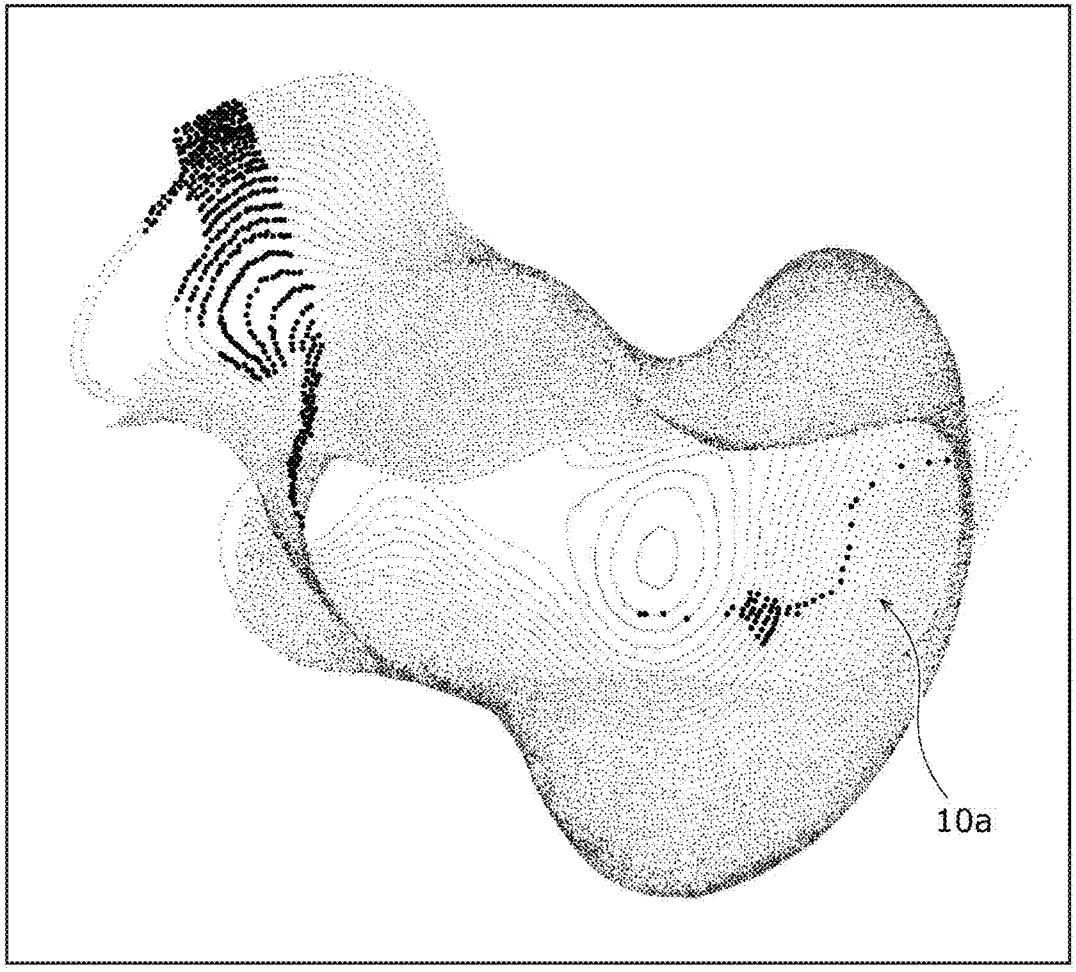
FIG. 10 is a diagram indicating another example of estimation information according to the embodiment.
Figure 11:
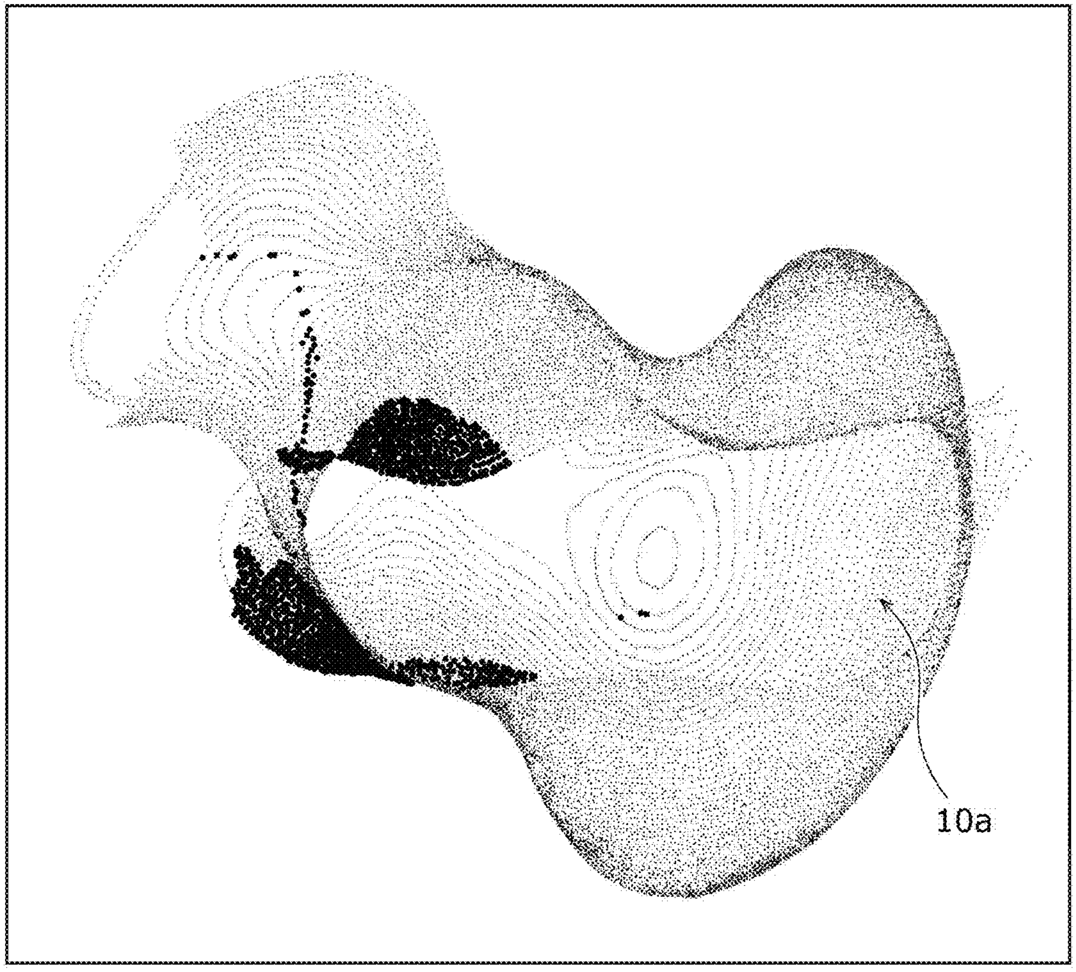
FIG. 11 is a diagram indicating another example of estimation information according to the embodiment.
Figure 12:
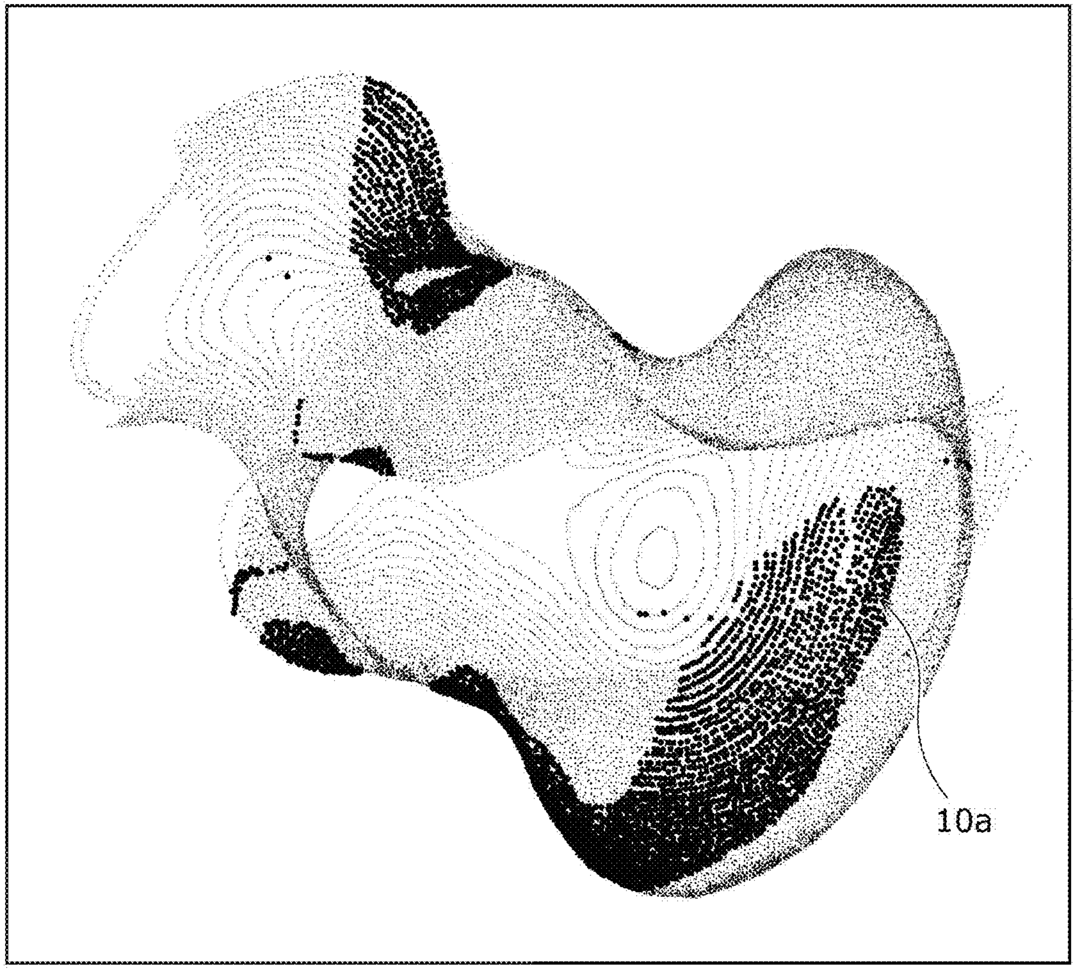
FIG. 12 is a diagram indicating another example of estimation information according to the embodiment.
Figure 13:
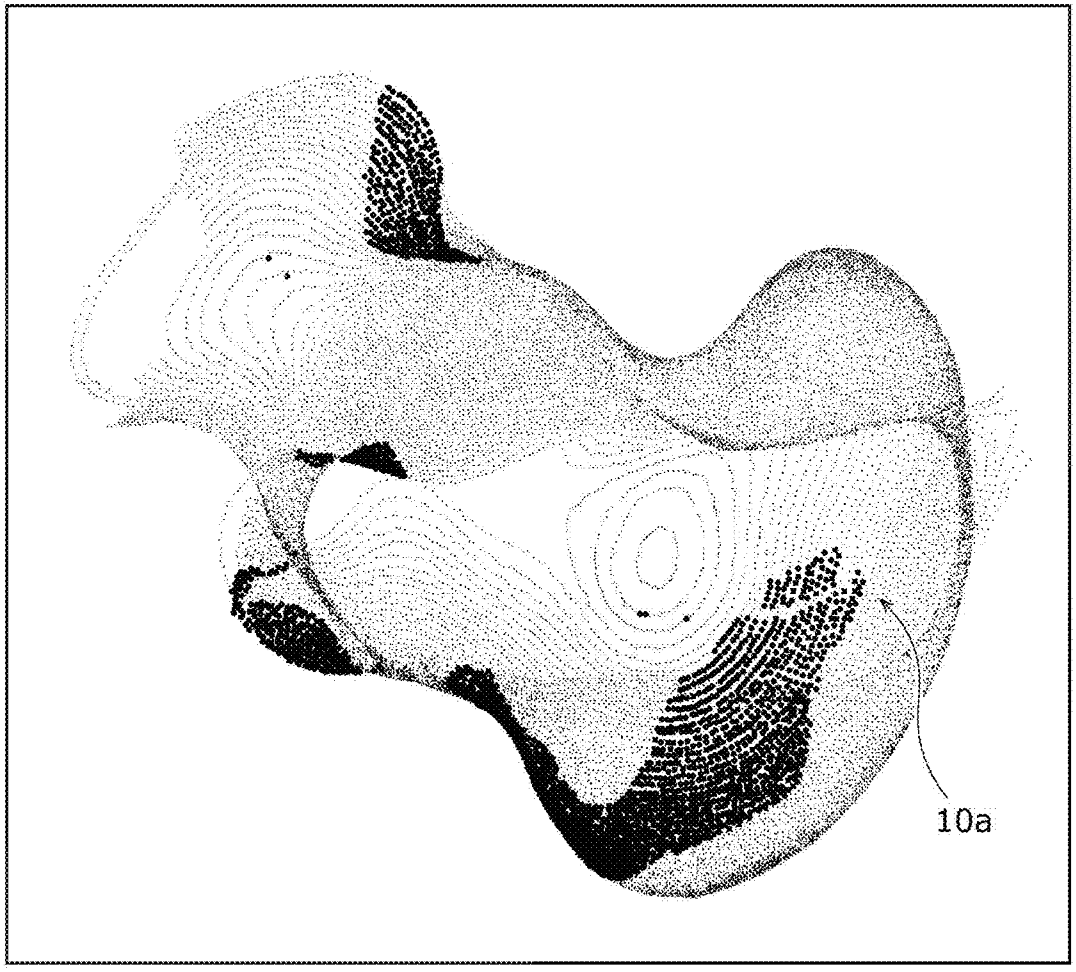
FIG. 13 is a diagram indicating another example of estimation information according to the embodiment.
Figure 14:
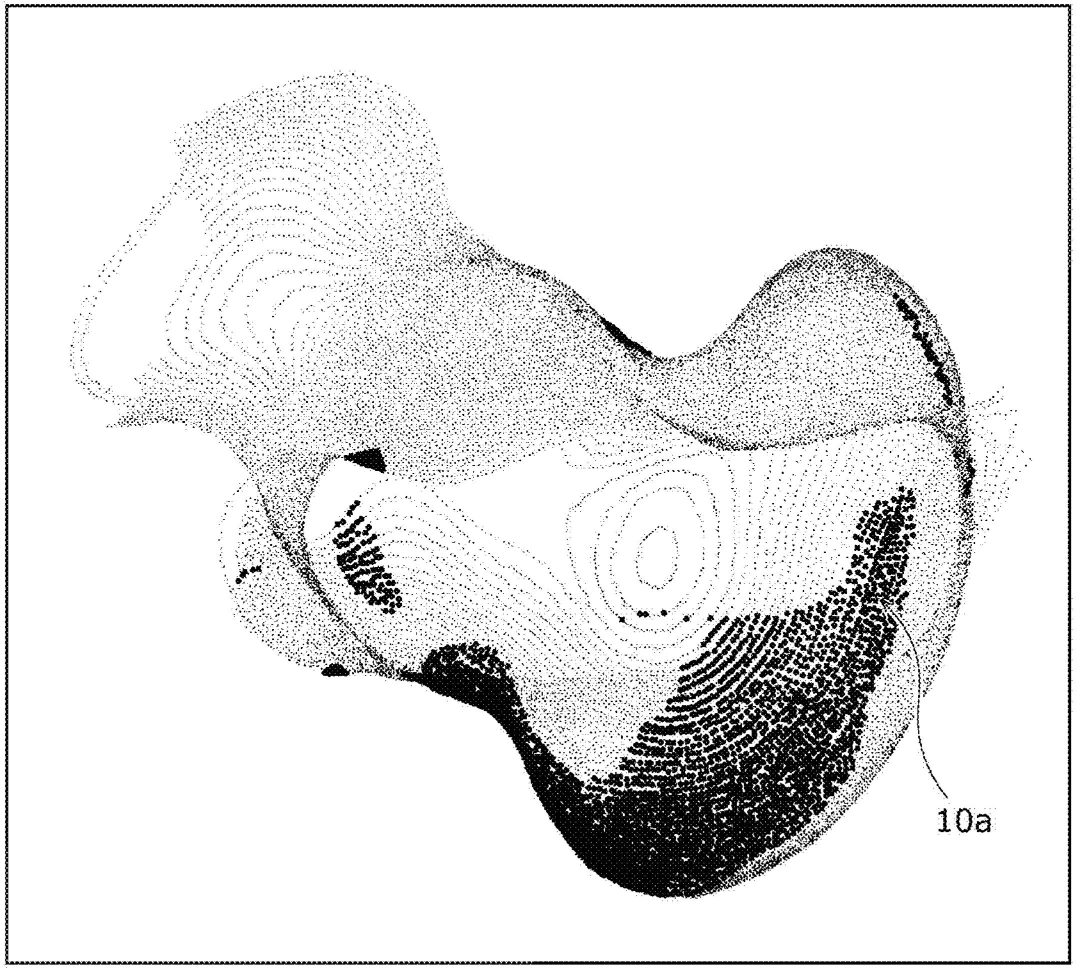
FIG. 14 is a diagram indicating another example of estimation information according to the embodiment.
Figure 15:
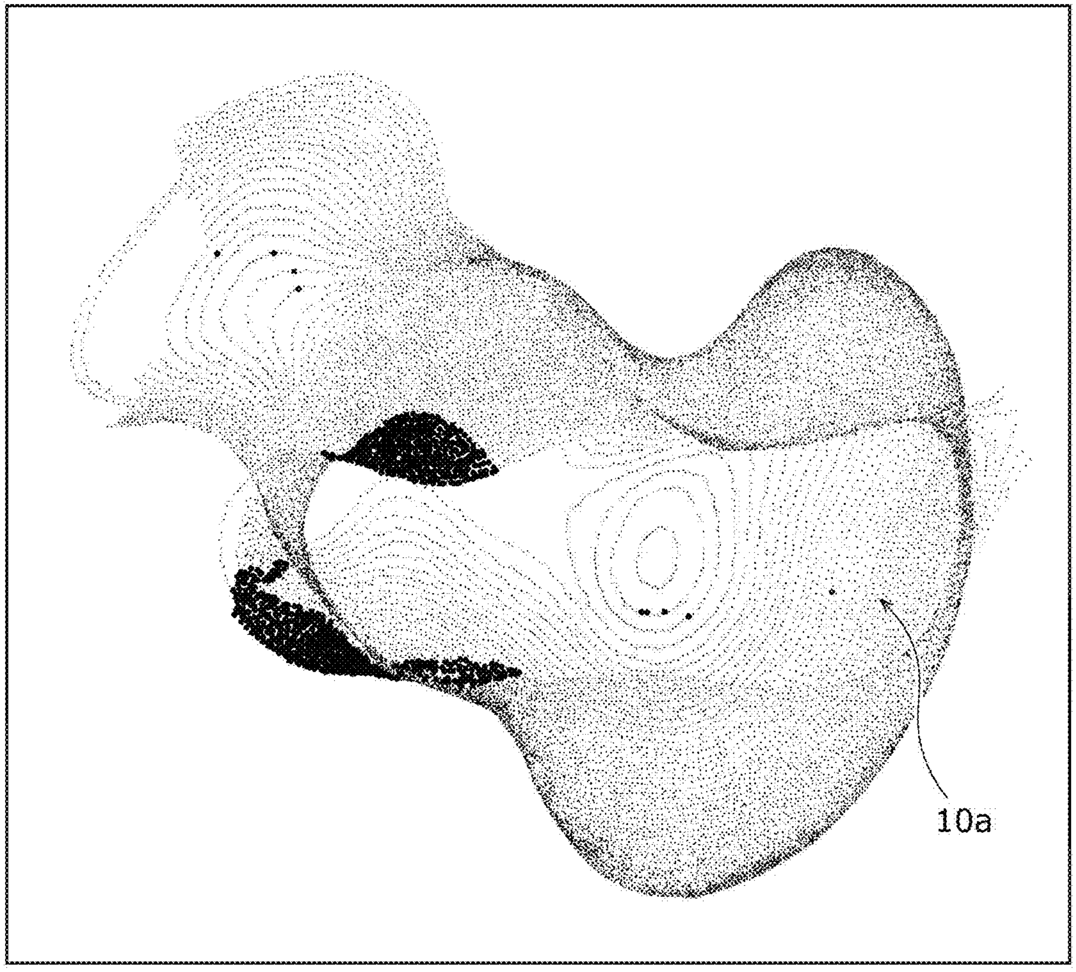
FIG. 15 is a diagram indicating another example of estimation information according to the embodiment.
Figure 16:
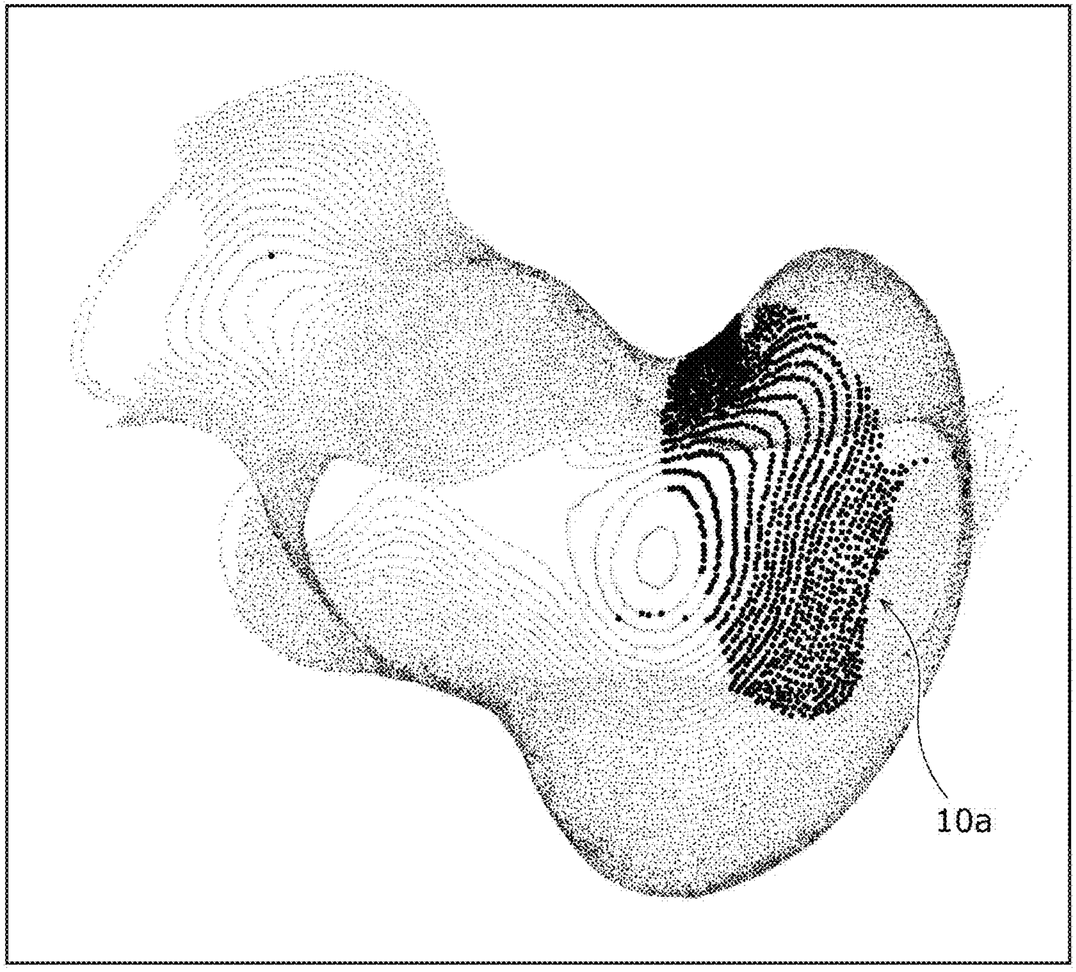
FIG. 16 is a diagram indicating another example of estimation information according to the embodiment.

FIG. 9 is a diagram indicating an example of estimation information according to the embodiment.

More specifically, FIG. 9 is a schematic diagram of image data indicating the relationship between the shape of cerebral aneurysm 10*a* and the maximum main strain. The relationship is an example of the estimation information. In FIG. 9, a large dot or a small dot is assigned to the portion corresponding to each of the plurality of points in cerebral aneurysm 10*a*, and the shape of cerebral aneurysm 10*a* is indicated by these two kinds of dots. It is to be noted that large dots correspond to predetermined points at each of which the maximum main strain which expands by a predetermined rate or more has occurred, and small dots correspond to points other than the points corresponding to the large dots. In addition, although the large dots or small dots are illustrated in the image data in FIG. 9, the sizes of the plurality of predetermined dots in the organ wall or the blood vessel wall (here, aneurysm wall 11) used to generate the behavioral information are the same.

FIGS. 10 to 16 are each a diagram indicating another example of estimation information according to the embodiment. In each of FIGS. 10 to 16, the shape of cerebral aneurysm 10*a* is indicated by large dots and small dots as in FIG. 9.

In addition, the maximum main strain which changes over time is illustrated in the order from FIGS. 9 to 16. The maximum main strains in cerebral aneurysm 10*a* in the above diagrams are obtained: in Step 0 in the case of FIG. 9; in Step 10 in the case of FIG. 10; in Step 20 in the case of FIG. 11; in Step 30 in the case of FIG. 12; in Step 40 in the case of FIG. 13; in Step 50 in the case of FIG. 14; in Step 60 in the case of FIG. 15; and in Step 70 in the case of FIG. 16. In other words, the estimation information indicated in each of FIGS. 9 to 16 indicates the changes over time in the shape of the cerebral aneurysm in the case and the predetermined points at which the maximum main strains that expand by the predetermined rate occur.

Furthermore, cerebral aneurysm 10*a* has been subjected to craniotomy. The shape of the cerebral aneurysm and the region in which the blood vessel wall is thin are shown through craniotomy.

Here, the shape of the cerebral aneurysm and the region in which the blood vessel wall is red shown through the craniotomy are compared with each other. It is to be noted that the red region corresponds to a region in which the blood vessel wall is fragile or thin. As a result, it is indicated that the predetermined point at which the maximum main strain which expands by the predetermined rate or more indicated by the estimation information has occurred corresponds to the red region in the blood vessel wall (the region in which the blood vessel wall is fragile or thin).

In this way, the red region may correspond to a thin region. In other words, the inventors' hypothesis that the calculated strain (here, the maximum main strain) and the thickness of the organ wall or the thickness of the blood vessel wall have a correlation is indicated to be correct.

As described above, the estimation information which is information in which the calculated strain (here, the maximum main strain) can be used as highly precise information about the thickness of the blood vessel wall.

Such information is useful information for, for example, discriminating a cerebral aneurysm which is likely to grow and rapture and a cerebral aneurysm which is unlikely to grow and rapture, and appropriately determining the necessity of treatment.

In other words, the wall thickness estimation method according to this embodiment makes it possible to propose useful information for providing a specific treatment for a disease of a blood vessel by generating highly accurate information about a wall of the blood vessel according to a minimally invasive method. Furthermore, the wall thickness estimation method according to this embodiment can be used to estimate the thickness of an organ wall without being limited to the thickness of the blood vessel wall.

In other words, the wall thickness estimation method according to this embodiment makes it possible to propose useful information for providing a specific treatment for a disease of an organ by generating highly accurate information about a wall of the organ according to a minimally invasive method in which no abdominal operation, open heart surgery, craniotomy, etc., are used.

Advantageous Effects, Etc.

As described above, the wall thickness estimation method includes obtaining step S101, generating step S102, and outputting step S103. Obtaining step S101 is a step of obtaining behavioral information based on a video in which an organ wall or a blood vessel wall is captured using four-dimensional angiography. The behavioral information is numerical information about changes over time in the position of each of a plurality of predetermined points in the organ wall or the blood vessel wall. Generating step S102 is a step of generating, based on the behavioral information obtained in obtaining step S101, estimation information that visualizes the strain of each of the plurality of predetermined points for estimating a thickness of the organ wall or a thickness of the blood vessel wall. Outputting step S103 is a step of outputting the estimation information generated in generating step S102.

Furthermore, a computer program according to this embodiment causes a computer to execute the above-described wall thickness estimation method.

In this way, in the wall thickness estimation method, for example, a video in which the blood vessel wall is captured is generated using the X-ray CT device or the MRI device, and four-dimensional angiography. For example, the video in which the blood vessel is captured is obtained using a minimally invasive method compared with methods such as craniotomy. The wall thickness estimation method makes it possible to generate estimation information that visualizes the strain of each of the plurality of predetermined points for estimating the thickness of the blood vessel wall, using the behavioral information related to the video. It is shown that the thickness of the blood vessel wall estimated based on the estimation information corresponds to the thickness of the blood vessel wall obtained by craniotomy.

In other words, the wall thickness estimation method can generate highly accurate information about the wall thickness in the vicinity of each of the plurality of predetermined points in the blood vessel wall. In this embodiment, for example, the thickness of aneurysm wall 11 of cerebral aneurysm 10 is estimated. Such information is useful information for, for example, discriminating a cerebral aneurysm which is likely to grow and rapture and a cerebral aneurysm which is unlikely to grow and rapture, and appropriately determining the necessity of treatment.

It is to be noted that the wall thickness estimation method can be used to estimate the thickness of an organ wall without being limited to the thickness of the blood vessel wall.

In other words, the wall thickness estimation method according to this embodiment makes it possible to propose useful information for providing a specific treatment for a disease of an organ or a disease of a blood vessel by generating highly accurate information about a wall of the organ or a wall of the blood vessel according to a minimally invasive method.

In addition, in the wall thickness estimation method, the thickness of the blood vessel wall is a thickness of a wall of an aneurysm or a thickness of a wall of a varicose vein.

In this way, the wall thickness estimation method can estimate the thickness of the wall of the aneurysm or the thickness of the wall of the varicose vein as the thickness of the blood vessel wall.

In addition, in the wall thickness estimation method, the thickness of the blood vessel wall is a thickness of a wall of a cerebral aneurysm.

In this way, the wall thickness estimation method can estimate the thickness of the wall of the cerebral aneurysm as the thickness of the blood vessel wall.

In addition, in the wall thickness estimation method, the thickness of the blood vessel wall is a thickness of the blood vessel wall of an artery or a thickness of the blood vessel wall of a vein.

In this way, the wall thickness estimation method can estimate the thickness of the blood vessel wall of the artery or the thickness of the blood vessel wall of the vein as the thickness of the blood vessel wall.

Wall thickness estimation device 100 includes obtainer 110, generator 120, and outputter 130. Obtainer 110 obtains behavioral information which is numerical information about changes over time in position of each of a plurality of predetermined points in an organ wall or a blood vessel wall, based on a video in which the organ wall or the blood vessel wall is captured obtained using four-dimensional angiography. Generator 120 generates, based on the behavioral information obtained by obtainer 110, estimation information that visualizes the strain of each of the plurality of predetermined points for estimating a thickness of the organ wall or a thickness of the blood vessel wall. Outputter 130 outputs the estimation information generated by generator 120.

In this way, in wall thickness estimation device 100, for example, a video in which the blood vessel wall is captured is generated using (i) the X-ray CT device or the MRI device and (ii) four-dimensional angiography. For example, the video in which the blood vessel is captured is obtained using a minimally invasive method compared with methods such as craniotomy. Wall thickness estimation device 100 is capable of generating estimation information that visualizes the strain of each of the plurality of predetermined points for estimating the thickness of the blood vessel wall, using the behavioral information related to the video. It is shown that the thickness of the blood vessel wall estimated based on the estimation information corresponds to the thickness of the blood vessel wall obtained by craniotomy.

In other words, wall thickness estimation device 100 is capable of generating highly accurate information about the wall thickness in the vicinity of each of the plurality of predetermined points in the blood vessel wall. In this embodiment, for example, the thickness of aneurysm wall 11 of cerebral aneurysm 10 is estimated. Such information is useful information for, for example, discriminating a cerebral aneurysm which is likely to grow and rapture and a cerebral aneurysm which is unlikely to grow and rapture, and appropriately determining the necessity of treatment.

It is to be noted that wall thickness estimation device 100 can be used to estimate the thickness of an organ wall without being limited to the thickness of the blood vessel wall.

In other words, wall thickness estimation device 100 according to this embodiment is capable of proposing useful information for providing a specific treatment for a disease of an organ or a disease of a blood vessel by generating highly accurate information about a wall of the organ or a wall of the blood vessel according to a minimally invasive method.

Furthermore, wall thickness estimation system 1000 includes: wall thickness estimation device 100; video information processing device 300 which obtains the video, generates the behavioral information, and outputs the behavioral information to obtainer 110; and display 200 which displays the estimation information output by outputter 130.

In this way, in wall thickness estimation system 1000, for example, a video in which the blood vessel wall is captured is generated using the X-ray CT device or the MRI device, and four-dimensional angiography. For example, the video in which the blood vessel is captured is obtained using a minimally invasive method compared with methods such as craniotomy. Wall thickness estimation system 1000 is capable of generating estimation information that visualizes the strain of each of the plurality of predetermined points for estimating the thickness of the blood vessel wall, using the behavioral information related to the video. It is shown that the thickness of the blood vessel wall estimated based on the estimation information corresponds to the thickness of the blood vessel wall obtained by craniotomy.

In other words, wall thickness estimation system 1000 is capable of generating highly accurate information about the wall thickness in the vicinity of each of the plurality of predetermined points in the blood vessel wall. In this embodiment, for example, the thickness of aneurysm wall 11 of cerebral aneurysm 10 is estimated. Such information is useful information for, for example, discriminating a cerebral aneurysm which is likely to grow and rapture and a cerebral aneurysm which is unlikely to grow and rapture, and appropriately determining the necessity of treatment.

It is to be noted that wall thickness estimation system 1000 can be used to estimate the thickness of an organ wall without being limited to the thickness of the blood vessel wall.

In other words, wall thickness estimation system 1000 according to this embodiment is capable of proposing useful information for providing a specific treatment for a disease of an organ or a disease of a blood vessel by generating highly accurate information about a wall of the organ or a wall of the blood vessel according to a minimally invasive method.

Furthermore, by means of estimation information being visualized and displayed, for example, a doctor, etc., can obtain the highly accurate information about the thickness of the organ wall or the thickness of the blood vessel wall.

Other Embodiments

Although the wall thickness estimation method and the like according to the embodiment have been described above, the present invention is not limited to the above embodiment.

It is to be noted that large dots correspond to predetermined points at each of which the maximum main strain which expands by a predetermined rate or more has occurred. As one example, the large dots correspond to predetermined points at each of which the maximum main strain which expands by 5% or more relative to the size of the above-described minute cube corresponding to the respective predetermined points has occurred. It is to be noted that the predetermined rate may be 5% as described above, 10%, or 15%. In addition, the predetermined rate is not limited thereto, and may be another rate.

In addition, although the maximum main strain is used as a strain to output the estimation information in the embodiment, the maximum main strain is a non-limiting example.

For example, the two main strains other than the maximum main strain among the vertical strains of three components may be used. In other words, assuming that the main strain having the minimum value among the vertical strains (main strains) of the three components is the minimum main strain, and that the main strain having the intermediate value between the minimum value of the main strain and the maximum value of the main strain among the vertical strains (main strains) of the three components is the intermediate main stain, the minimum strain or the intermediate strain may be used as a strain to output estimation information.

Furthermore, although the main strain is used as the strain in the embodiment, the main strain is a non-limiting example.

For example, one strain among the strains of the nine components in total including the vertical strains of the three components and the sharing strains of the six components may be used as a strain to output estimation information.

In addition, for example, an engineering strain, a stretch, or a logarithmic strain may be used to output estimation information.

The engineering strain is one example of strains that are calculated from behavioral information. In addition, the stretch is one example of parameters relating to strains that are calculated from an engineering strain. In addition, the logarithmic strain is one example of strains that are calculated from behavioral information.

In this way, a strain other than the maximum main strain indicated in the embodiment may be used to output estimation information.

In addition, in the embodiment, the absolute value of a strain is calculated as the value of the strain relating to the thickness of the organ wall or the thickness of the blood vessel wall. For this reason, when knowledge of cases is accumulated, it is possible to estimate the likelihood of rapture (the degree of the risk of rapture) of the organ wall or the blood vessel wall.

The above embodiment describes methods of obtaining behavioral information using actual cases and four-dimensional angiography. However, the methods of obtaining the behavioral information are not limited to these examples. For example, the behavioral information may be obtained by first and second other exemplary methods described below.

In a first other exemplary method, behavioral information is obtained by using an artificial aneurysm that has been artificially created, an artificial heart connected to the artificial aneurysm, and an imaging device.

An artificial aneurysm is an artificial aneurysm that has occurred in an artificial blood vessel. The artificial blood vessel and the artificial aneurysm are created to mimic a human blood vessel and a human aneurysms that has occurred in the human blood vessel. The artificial aneurysm may be made of, for example, a rubber material. For example, a silicone rubber, a fluorine rubber, or the like may be used.

The artificial aneurysm may also be made of, for example, a silicone resin. As long as the artificial aneurysm is made of a flexible material, the material used for the artificial aneurysm is not limited to the above examples.

The artificial aneurysm is created utilizing image data obtained by an X-ray CT device or an MRI device as described above. This image data includes data on the human blood vessel and the aneurysm that has occurred in the blood vessel.

The artificial aneurysm is created based on digital imaging and communications in medicine (DICOM) data related to the image data obtained above.

An artificial heart is a device that performs the pumping function of the human heart. The artificial heart and the artificial aneurysm are connected, and the artificial heart's pumping function is activated to cause the artificial aneurysm to move in a pulsating manner. The behavioral information is obtained using this movement of the artificial aneurysm and the imaging device.

The imaging device is, for example, a camera capable of capturing still images and videos. Alternatively, the imaging device may be a device capable of obtaining the following all pieces of information: three-dimensional coordinates on a surface of an observation target; and a displacement in the three-dimensional space. Such an imaging device is capable of obtaining all the pieces of information which are three-dimensional coordinates on a surface of an observation target, a displacement in the three-dimensional space, a speed in the three-dimensional space, and an acceleration in the three-dimensional space, by capturing a video for 1 second, 5 seconds, or 10 seconds. It is to be noted time duration at which the imaging device performs imaging is not limited thereto, and may be other time duration.

As described above, in the first other exemplary method, all the pieces of information which are the three-dimensional coordinates on the surface of the observation target and the displacement in the three-dimensional space are obtained by means of the imaging device capturing the video of the artificially created aneurysm that pulsates. Behavioral information may be obtained based on any or all of the above pieces of information among the three-dimensional coordinates on the surface of the observation target and the displacement in the three-dimensional space.

In the first other exemplary method according to the first other example, such behavioral information can be obtained more easily than in the craniotomy described above because the technique is less invasive.

In a second other exemplary method, a model animal having a blood vessel in which an aneurysm has occurred and the imaging device described above are used to obtain behavioral information.

More specifically, the imaging device images a blood vessel with an aneurysm in the model animal to obtain the following all pieces of information: three-dimensional coordinates in a three-dimensional space on the surface of the blood vessel with aneurysm in the model animal; and a displacement in the three-dimensional space. The behavioral information may be obtained based on any or all of the above pieces of information.

In the second other exemplary method, unlike a case involving a human as shown in the embodiment, a consent form and the like for the human subject of the case is not required. Additionally, since the surface of the blood vessel and aneurysm of the model animal can be patterned (for example, marked by spraying) for imaging, time evolution data of precise three-dimensional coordinates can be obtained.

Furthermore, data on the blood vessel and aneurysm of the model animal can be obtained at equal time intervals (for example, once every two weeks). This makes it easier to obtain behavioral information than in the embodiment.

The above method can be used to easily obtain a large number of pieces of behavioral information, and consequently, a large number of pieces of estimation information can be obtained. This is expected to improve the accuracy of the information about the wall.

Although the embodiment describes the thickness of the blood vessel wall as the thickness of aneurysm wall 11 of cerebral aneurysm 10, the thickness of the blood vessel wall may be the thickness of the wall of the blood vessel that is an artery or a vein, as described above. For example, when the thickness of the wall is the thickness of the wall of the blood vessel that is an artery or a vein, the degree of stenosis of the artery or the vein is estimated using the blood vessel wall thickness estimation method and the like according to the embodiment.

In each of the above embodiments, each element may be configured in the form of dedicated hardware or implemented by executing a software program suitable for the element. Each element may be implemented by means of a program executing unit, such as a central processing unit (CPU) or a processor, reading and executing a software program recorded on a recording medium such as a hard disk or semiconductor memory.

It is to be noted that embodiments resulting from variations of the above embodiments arrived at by those skilled in the art, as well as embodiments resulting from optional combinations of elements and functions in the above embodiments are included within the present invention as long as the embodiments do not depart from the scope of the present invention.

INDUSTRIAL APPLICABILITY

The wall thickness estimation method according to the present invention can be used in various applications, such as medical devices and medical methods.

The invention claimed is:

1. A wall thickness estimation method comprising:

obtaining behavioral information based on a video in which a blood vessel wall is captured using four-dimensional angiography, the behavioral information being numerical information about changes over time in a position of each of a plurality of predetermined points in the blood vessel wall;

generating, based on the behavioral information obtained in the obtaining step, estimation information that visualizes a strain of each of the plurality of predetermined points for estimating a thickness of the blood vessel wall; and outputting the estimation information generated in the generating step, wherein each of the plurality of predetermined points is regarded as a minute cube, wherein the generating the estimation information includes calculating, for each of the plurality of predetermined points, vertical strains of three components relative to a plurality of surfaces of the minute cube corresponding to the predetermined point, wherein for each of the plurality of predetermined points, the estimation information is information that visualizes, as the strain of the predetermined point, a strain having a maximum value among the vertical strains of the three components relative to the plurality of surfaces of the minute cube corresponding to the predetermined point, wherein the estimation information is image data indicating a relationship between (i) a shape of the blood vessel wall and (ii) the strain of each of the plurality of predetermined points, such that a first dot is assigned for each of the predetermined points at which the strain of the predetermined point expands by a predetermined rate or more and a second dot is assigned to the remaining plurality of predetermined points, the second dot being visually different from the first dot, and wherein the thickness of the blood vessel wall is a thickness of a wall of a cerebral aneurysm.

2. The wall thickness estimation method according to claim 1, further comprising wherein a treatment for a disease of a blood vessel having the blood vessel wall is determined using the outputted estimation information.

3. A non-transitory computer-readable recording medium having a program recorded thereon for causing a computer to execute a wall thickness estimation method comprising:

obtaining behavioral information based on a video in which an a blood vessel wall is captured using four-dimensional angiography, the behavioral information being numerical information about changes over time in a position of each of a plurality of predetermined points in the blood vessel wall;

generating, based on the behavioral information obtained in the obtaining step, estimation information that visualizes a strain of each of the plurality of predetermined points for estimating a thickness of the blood vessel wall; and outputting the estimation information generated in the generating step, wherein each of the plurality of predetermined points is regarded as a minute cube, wherein the generating the estimation information includes calculating, for each of the plurality of predetermined points, vertical strains of three components relative to a plurality of surfaces of the minute cube corresponding to the predetermined point, wherein for each of the plurality of predetermined points, the estimation information is information that visualizes, as the strain of the predetermined point, a strain having a maximum value among the vertical strains of the three components relative to the plurality of surfaces of the minute cube corresponding to the predetermined point, wherein the estimation information is image data indicating a relationship between (i) a shape of the blood vessel wall and (ii) the strain of each of the plurality of predetermined points, such that a first dot is assigned for each of the predetermined points at which the strain of the predetermined point expands by a predetermined rate or more and a second dot is assigned to the remaining plurality of predetermined points, the second dot being visually different from the first dot, and wherein the thickness of the blood vessel wall is a thickness of a wall of a cerebral aneurysm.

4. A wall thickness estimation device comprising:

an obtainer which obtains behavioral information based on a video in which a blood vessel wall is captured using four-dimensional angiography, the behavioral information being numerical information about changes over time in a position of each of a plurality of predetermined points in the blood vessel wall;

a generator which generates, based on the behavioral information obtained by the obtainer, estimation information that visualizes a strain of each of the plurality of predetermined points for estimating a thickness of the blood vessel wall; and an outputter which outputs the estimation information generated by the generator, wherein each of the plurality of predetermined points is regarded as a minute cube, wherein the generator generates the estimation information by calculating, for each of the plurality of predetermined points, vertical strains of three components relative to a plurality of surfaces of the minute cube corresponding to the predetermined point, wherein for each of the plurality of predetermined points, the estimation information is information that visualizes, as the strain of the predetermined point, a strain having a maximum value among the vertical strains of the three components relative to the plurality of surfaces of the minute cube corresponding to the predetermined point, wherein the estimation information is image data indicating a relationship between (i) a shape of the blood vessel wall and (ii) the strain of each of the plurality of predetermined points, such that a first dot is assigned for each of the predetermined points at which the strain of the predetermined point expands by a predetermined rate or more and a second dot is assigned to the remaining plurality of predetermined points, the second dot being visually different from the first dot, and wherein the thickness of the blood vessel wall is a thickness of a wall of a cerebral aneurysm.

5. A wall thickness estimation system comprising:

an obtainer which obtains behavioral information based on a video in which a blood vessel wall is captured using four-dimensional angiography, the behavioral information being numerical information about changes over time in a position of each of a plurality of predetermined points in the blood vessel wall;

a generator which generates, based on the behavioral information obtained by the obtainer, estimation information that visualizes a strain of each of the plurality of predetermined points for estimating a thickness of the blood vessel wall;

an outputter which outputs the estimation information generated by the generator;

a video information processing device which obtains the video, generates the behavioral information, and outputs the behavioral information to the obtainer; and a display which displays the estimation information output by the outputter, wherein each of the plurality of predetermined points is regarded as a minute cube, wherein the generator generates the estimation information by calculating, for each of the plurality of predetermined points, vertical strains of three components relative to a plurality of surfaces of the minute cube corresponding to the predetermined point, wherein for each of the plurality of predetermined points, the estimation information is information that visualizes, as the strain of the predetermined point, a strain having a maximum value among the vertical strains of the three components relative to the plurality of surfaces of the minute cube corresponding to the predetermined point, wherein the estimation information is image data indicating a relationship between (i) a shape of the blood vessel wall and (ii) the strain of each of the plurality of predetermined points, such that a first dot is assigned for each of the predetermined points at which the strain of the predetermined point expands by a predetermined rate or more and a second dot is assigned to the remaining plurality of predetermined points, the second dot being visually different from the first dot, and wherein the thickness of the blood vessel wall is a thickness of a wall of a cerebral aneurysm.

* * * * *